(12) United States Patent
Kennedy et al.

(10) Patent No.: US 10,980,407 B2
(45) Date of Patent: Apr. 20, 2021

(54) MEDICAL IMAGING SYSTEM

(71) Applicant: ARTHREX, INC., Naples, FL (US)

(72) Inventors: Bruce Laurence Kennedy, Santa Barbara, CA (US); David A. D'Alfonso, Gaviota, CA (US)

(73) Assignee: ARTHREX, INC., Naples, FL (US)

( * ) Notice: Subject to any disclaimer, the term of this patent is extended or adjusted under 35 U.S.C. 154(b) by 0 days.

(21) Appl. No.: 16/782,300

(22) Filed: Feb. 5, 2020

(65) Prior Publication Data

US 2020/0221940 A1    Jul. 16, 2020

Related U.S. Application Data

(62) Division of application No. 16/041,605, filed on Jul. 20, 2018, now Pat. No. 10,638,921.

(51) Int. Cl.
| | | |
|---|---|---|
| *A61B 1/05* | (2006.01) | |
| *A61B 1/06* | (2006.01) | |
| *H04N 5/225* | (2006.01) | |
| *G02B 23/24* | (2006.01) | |
| *A61B 1/00* | (2006.01) | |

(52) U.S. Cl.
CPC ............. *A61B 1/05* (2013.01); *A61B 1/0661* (2013.01); *A61B 1/00045* (2013.01); *G02B 23/2461* (2013.01); *G06T 2207/10068* (2013.01); *H04N 5/2256* (2013.01)

(58) Field of Classification Search
CPC ............ A61B 1/00002; A61B 1/00004; A61B 1/00009; A61B 1/00011; A61B 1/00018
See application file for complete search history.

(56) References Cited

U.S. PATENT DOCUMENTS

| | | |
|---|---|---|
| 5,335,662 A | 8/1994 | Kimura et al. |
| 5,428,386 A | 6/1995 | D'Alfonso et al. |
| 5,614,943 A | 3/1997 | Nakamura et al. |
| 5,743,647 A | 4/1998 | Nakamura et al. |
| 8,785,833 B2 | 7/2014 | Yabe et al. |
| 9,066,024 B2 | 6/2015 | Chang et al. |
| 9,101,287 B2 | 8/2015 | Levi et al. |
| 9,194,544 B2 | 11/2015 | Ono et al. |
| 9,270,919 B2 | 2/2016 | Amling et al. |
| 9,414,740 B2 | 8/2016 | Kennedy et al. |
| 9,800,853 B2 | 10/2017 | D'Alfonso et al. |
| 9,948,881 B2 | 4/2018 | Amling et al. |

(Continued)

FOREIGN PATENT DOCUMENTS

| | | |
|---|---|---|
| CN | 105769111 | 7/2016 |
| KR | 2017/0095008 | 8/2017 |

(Continued)

OTHER PUBLICATIONS

Int'l Search Report and Written Opinion—PCT/US2019/042374—dated Oct. 16, 2019—8 pgs.

*Primary Examiner* — Alexandra L Newton
(74) *Attorney, Agent, or Firm* — Karish & Bjorgum, PC

(57) ABSTRACT

A medical imaging system includes multiple illuminating endoscopes with cameras having image sensors exposure control and a frame memory. The exposure control of each camera activates the frame memory and light source for collection of selected frame images by the frame memory. A data link among the endoscopes synchronizes exclusive initiation of the exposure controls in recurring serial order for activation of each respective frame memory and light source.

3 Claims, 18 Drawing Sheets

(56) References Cited

U.S. PATENT DOCUMENTS

| | | |
|---|---|---|
| 2004/0183908 A1 | 9/2004 | Tominaga et al. |
| 2014/0052004 A1 | 2/2014 | D'Alfonso et al. |
| 2014/0139130 A1 | 5/2014 | Upton |
| 2014/0180001 A1 | 6/2014 | Von Grunberg et al. |
| 2014/0364690 A1 | 12/2014 | Seto |
| 2015/0094530 A1 | 4/2015 | Moriya |
| 2016/0073855 A1 | 3/2016 | Farr et al. |
| 2017/0013193 A1 | 1/2017 | Cogal et al. |

FOREIGN PATENT DOCUMENTS

| | | |
|---|---|---|
| WO | WO2014/028758 | 2/2014 |
| WO | WO2016/208664 | 12/2016 |

MEDICAL IMAGING SYSTEM

BACKGROUND OF THE INVENTION

The field of the present invention is medical video imaging.

Video imaging in surgery and other medical procedures has become quite common as minimally invasive endoscopic techniques have replaced previously used open approaches to treat patients. Such imaging is very advantageous for endoscopic joint surgery, particularly in the knee and shoulder. Such surgery can additionally benefit from two or more simultaneous endoscope camera views. Where joint surgery requires that the camera move repeatedly between portals, multiple cameras can reduce surgery time. Other orthopedic applications where a rigid endoscope is now used may benefit from a second view reachable only by a small diameter needle endoscope. Using multiple endoscopes at the same time can be useful. However, most endoscopes are coupled to a camera to collect the image and also to a light source for illumination. Should one endoscope be directed toward another, the illumination from the one can spoil the other's image. Additionally, some endoscope cameras control the lighting as part of their automatic exposure system. If lighting comes from another source, a camera auto exposure system may not be able to maintain the correct image brightness.

Endoscopic video systems have included an endoscope, camera, light source, and display. The camera is comprised of a camera control unit (CCU) and an image sensor. These system components have been arranged in different ways depending on the application. For example, the image sensor may be placed at the distal tip of the endoscope and the light source located in the endoscope handle. A large high-performance image sensor may be placed in a camera head enclosure attached to the proximal endoscope eyepiece and the light delivered to the endoscope through glass fibers from a remote light source.

SUMMARY OF THE INVENTION

The present invention is directed to video imaging systems that provide for the use of multiple video cameras with illumination in a medical procedure at the same time.

Method and apparatus are disclosed coordinating the timing of image capture and illumination of multiple endoscopes. Each can be made to video capture without others degrading the display. In doing this, the images being captured are not compromised by interfering illumination. At the same time, real time sequential images from multiple endoscopes may be separately displayed. The timing is coordinated such that only the light source associated with one endoscope is fully illuminated for image exposure during image capture from the associated endoscope. Background illumination may be provided in a second mode from another light source not from the light source then fully illuminated. By effecting image capture with each endoscope in serial order, multiple video displays from the endoscopes can run concurrently.

Accordingly, it is a principal object of the present invention to provide a system for advantageous employment of multiple illuminated video cameras in medical procedures. Other and further objects and advantages will appear hereinafter.

In the following description of the preferred embodiments, reference is made to the accompanying drawings which show by way of illustration specific embodiments in which the invention may be practiced. Wherever possible, the same reference numbers will be used throughout the drawings to refer to the same or like parts.

DETAILED DESCRIPTION OF THE PREFERRED EMBODIMENTS

Figure 1:
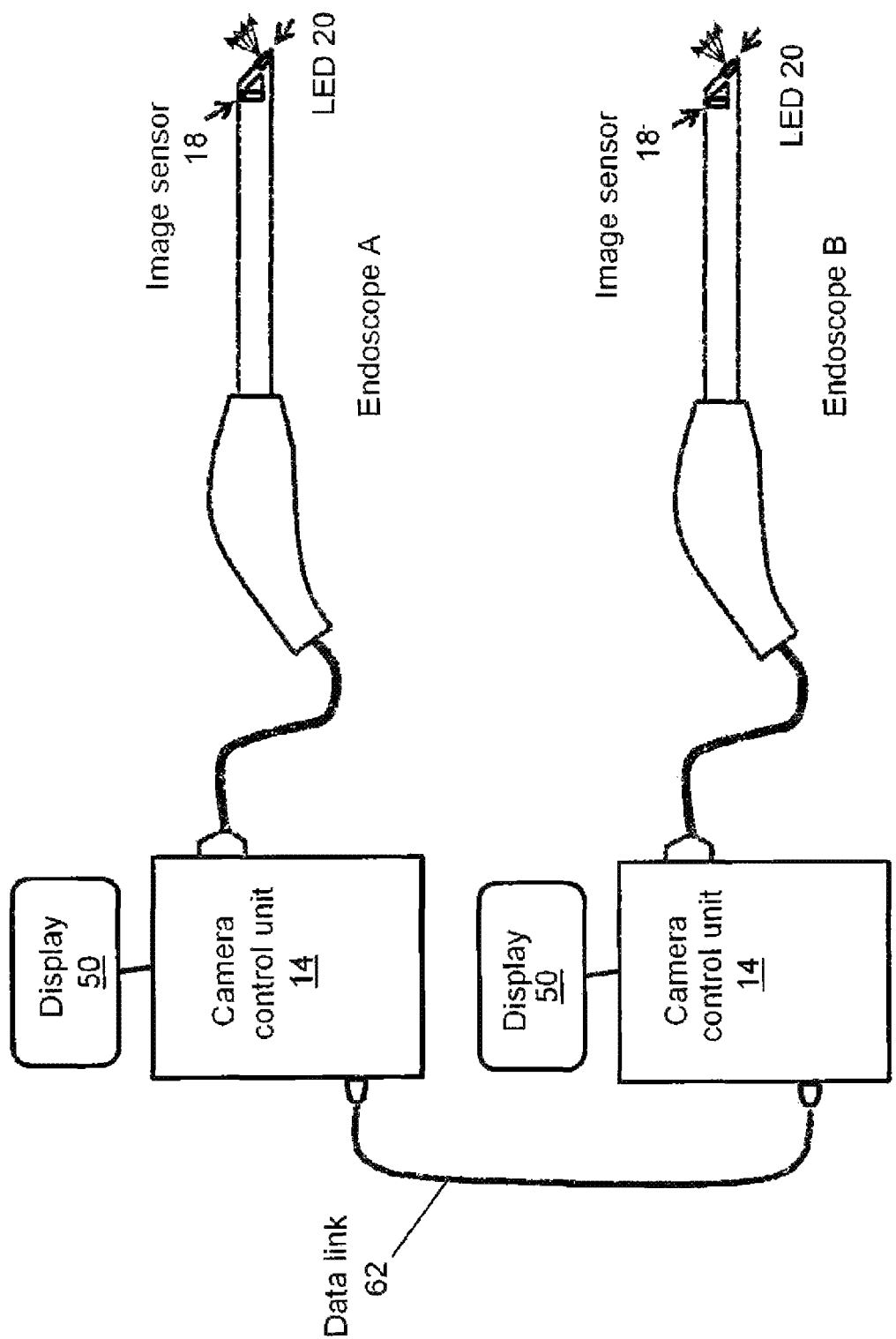
FIG. 1 is a schematic diagram of an endoscope system.
Figure 2:
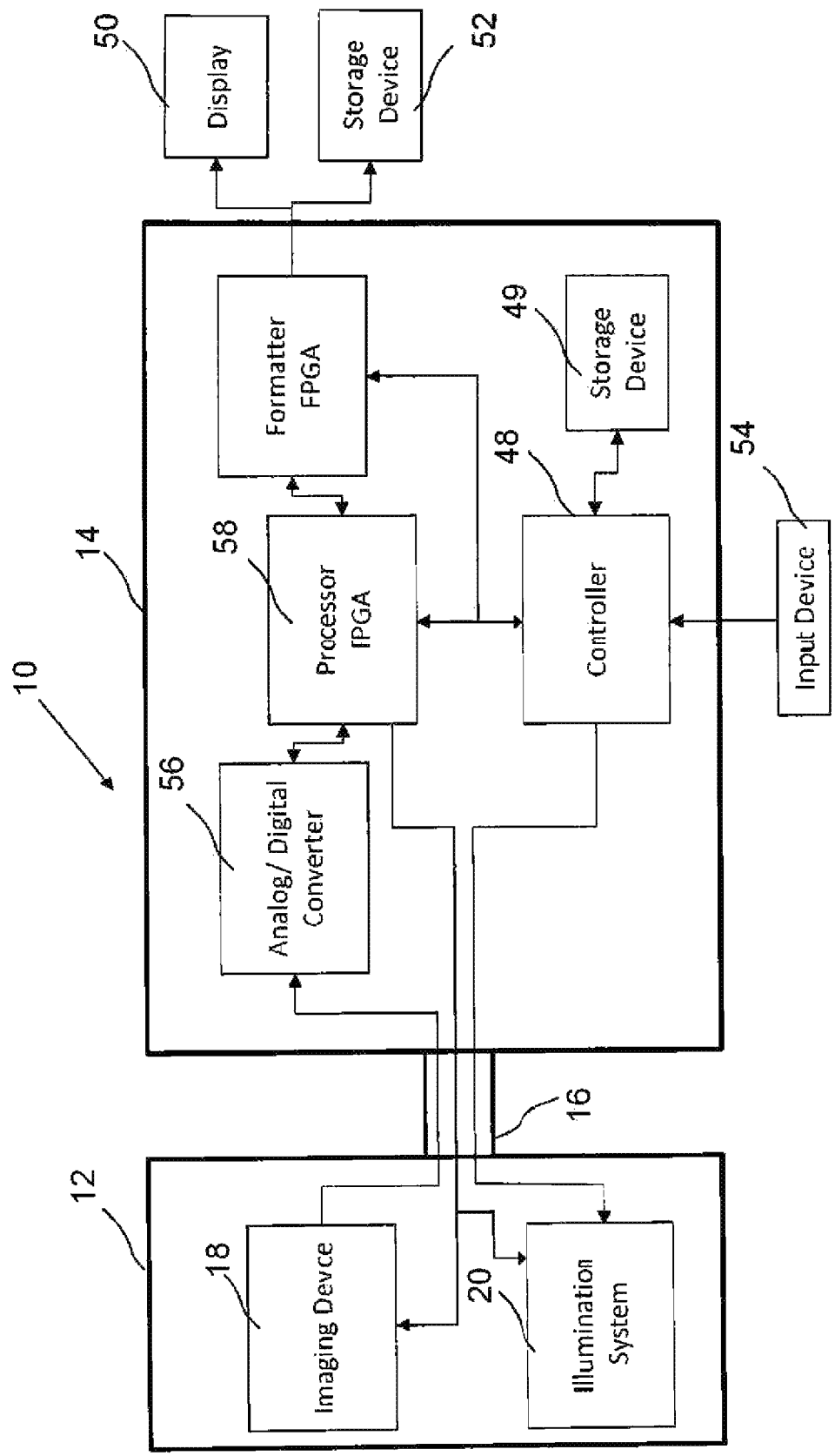
FIG. 2 is schematic diagram of a video camera system and an illumination system.
Figure 3:
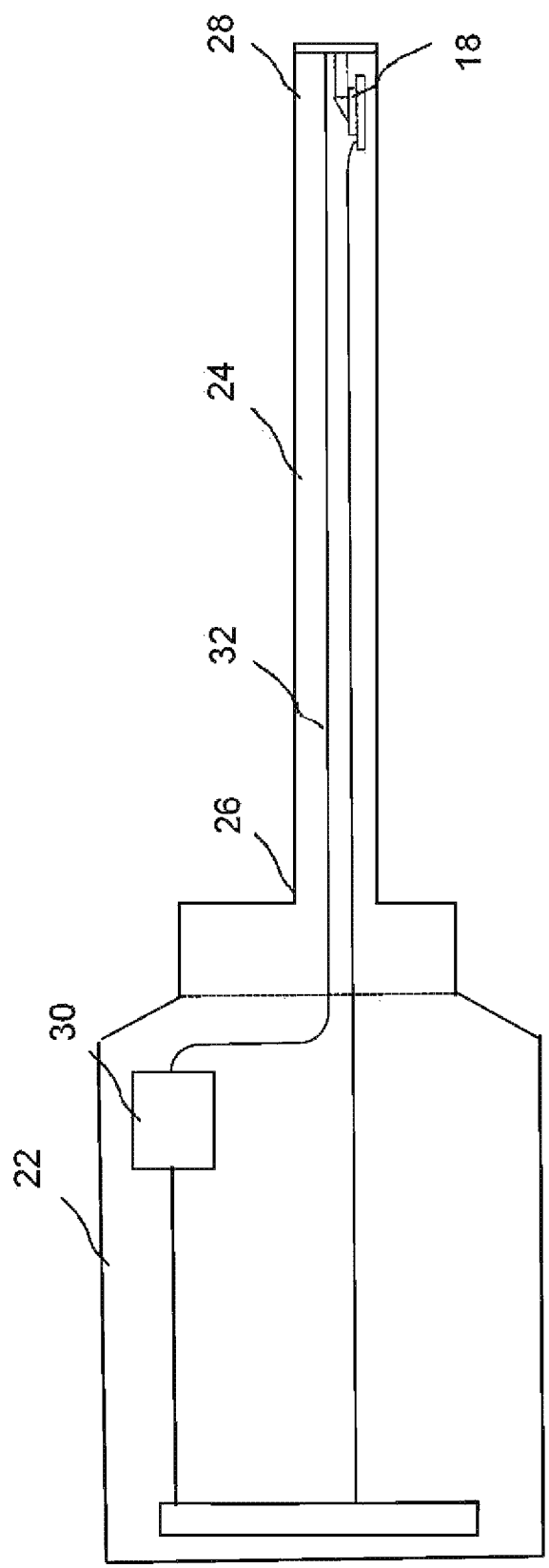
FIG. 3 is a schematic of an endoscope head.

FIG. 1 illustrates a duel endoscope system with a data link. FIG. 2 schematically illustrates an endoscopic camera 10 such as may be employed in the present embodiment and is generally characterized. Such endoscopic cameras may also be used individually. In the preferred embodiment, each is data linked for use in cooperation with one or more other endoscopic cameras. FIG. 3 schematically illustrates the distal end of an endoscope with camera and lighting components. Various kinds of endoscopes are contemplated for use in the preferred embodiment. The endoscopes used in any given system may be identical or disparate as are the camera choices.

In FIG. 2 an exemplar endoscopic camera 10 used in this embodiment has a video camera head 12 and a camera control unit 14. The video camera head 12 is coupled to the camera control unit 14 via a cable 16 to facilitate data transfer between the video camera 12 and the camera control unit 14. The camera alternatively may be wirelessly coupled to the camera control unit 14 such as via IEEE 802.11b, or IEEE 802.11n or ultra-wide band (UWB).

The video camera head 12 acquires image data and transmits it to the camera control unit 14 to process a usable image. Traditionally a charge coupled device (CCD) or a complementary metal oxide semiconductor (CMOS) is used as an image sensor 18. A CCD based video camera employs a global shutter image sensor; and a CMOS based video camera employs either a global shutter or a rolling shutter sensor. Further, CMOS rolling shutter sensors can incorporate global reset. The image sensor may be located at the distal end of an endoscope. From this group of shutter types, similar or dissimilar types may be used together in an individual system, Referring specifically to FIG. 3, the endoscope schematically illustrated has a light source 20, a housing 22 and a shaft 24 coupled to the housing 22. The shaft 24 has a proximal end 26 adjacent to the housing 22 and a distal end 28 for insertion into a body or other area to be viewed. The image sensor 18 is shown in this embodiment to be located at the distal end 28 and is understood to include an imaging optical assembly to receive detail in the illuminated field of view. The image sensor 18 may also be placed at a distance from the distal end of the endoscope with lenses therebetween. Indeed, the camera 10 and the light source 20 are contemplated to be systems more or less physically arranged with the endoscope. The camera 10 defines a field of view from the distal end of the endoscope; and the light source 20 illuminates that field of view regardless of the physical association.

The light source 20 includes a lamp 30. The lamp 30 is traditionally a semiconductor light source such as laser or LED to require low power and provide rapid activation to illuminate the field of view of the endoscopic camera 10. A light guide 32 is shown in FIG. 3 to be optically coupled to the lamp 30. As will be appreciated by one of skill in the art, the lamp 30 may be located with or without other components when a light guide 32 is employed or may be miniaturized at the distal end of the endoscope. All configurations of the light source 20 are to appropriately illuminate the field of view of the video camera. Further, the light generated as well as camera sensitivity may extend beyond the visible spectrum. The illumination may be intended to excite fluorescence directly in the target, or in a fluorescent substance such as indocyanine green, that is then sensed by the camera. For example, the light source might produce illumination in the near infrared (NIR) range and the camera sense the fluorescence at a longer IR wavelength. The illumination and camera sensitivity could extend from UV to NIR continuously or be composed of separate narrow bands.

Referring specifically to FIG. 2, the camera control unit 14 is preferably a programmable unit containing sufficient processing capacity to accommodate a wide range of control, user interface and image acquisition/processing functions. The camera control unit 14 has a controller 48 and runs program applications providing for a variety of capabilities. For instance, an image capture and display capability allows for both display of a live feed of an image through an image display 50 coupled to the camera control unit 14, as well as image capture. Captured images may also be stored or transmitted to other devices.

Timing in video cameras must be very precise and consistent. Software code executing on a processor is typically nondeterministic and therefore unable to produce the needed consistent operation. Instead field programmable gate arrays (FPGA) are preferred to control and process the output from image sensors. All processing steps of the video image are preferably done with an FPGA to achieve the required real time precise timing needed to generate a standard video output signal. In an endoscopic video system user interface logic and possible external network connectivity might be performed by software running on a processor.

In a current embodiment, analog RGB data is transmitted from the image sensor 18 to the camera control unit 14. The Analog RGB data passes through an Analog/Digital converter 56 to an FPGA 58 where the video is processed. The processed video is then passed to a video output 60 that may include a formatter FPGA where the video is formatted into various display formats. The formatter FPGA may also overlay information, such as patient and/or doctor information, onto the video. The formatted video may be converted back to an analog signal for display. The formatted video is sent to the display 50 and/or the storage device 52. Alternatively, an Analog/Digital converter may be located in the camera head and digital RGB data transmitted from the camera head 12 to the camera control unit 14. Additionally, the imaging device 18 itself may include an Analog/Digital converter.

The camera control unit 14 issues commands to the camera head 12 to adjust its operating characteristics, and the camera head 12 may send confirmation to the camera control unit 14 that it received the commands. The processor FPGA 58 and/or the controller 48 may communicate with a shutter driver either in the camera control unit 14 or the camera head 12 to control the exposure period of the imaging device. The image sensor 18 employed with the camera 10 must be accommodated as to choice of frame rate, pixel rate, number of horizontal lines per frame, pixels per line, type of color representation, image aspect ratio. For example, the image sensor may be a single row and column array with color filters applied over individual pixels in a Bayer pattern or multiple sensors mounted on a wavelength separating prism. If there is more than a single type of sensor that can be used with a camera system then a choice from a predetermined set of these settings is made to match the sensor. When a camera operates in standalone mode, that is by itself before another camera responds on the data link, the frame rate is determined by the time it takes to scan all the pixels. Assume the sensor pixel rate is 148.5 Mpix/sec and the number of lines is 1125 and the pixels per line is 2200. 1125×2200=2.475 Mpixels per frame so that 148.5/2.475=60 frames per second. The actual number of active image pixels per frame is fewer because of dark reference lines and pixels as well as intentional blanking time. For example, in a standard HDTV frame there are 1920 pixels per line×1080 vertical lines in each image frame. Additionally, the processor FPGA 58 and/or the controller 48 communicates with a light source 20 either in the camera control unit 14 or the camera head 12 to control the drive current to the lamp 30 of the light source 20.

FIGS. 1 and 2 illustrate the functional aspects of a dual camera and illumination system associated with two endoscopes. The video cameras 10A and 10B are coupled through a data link 62 therebetween. The controller 48 and processor 58 of the exemplar camera 10 of FIG. 2 may share or trade functions depending on the design. The data link 62 provides vs$_y$nc and sensor type, frame rate, frame timing and light timing between cameras 10, providing a video capture profile.

Figure 4:
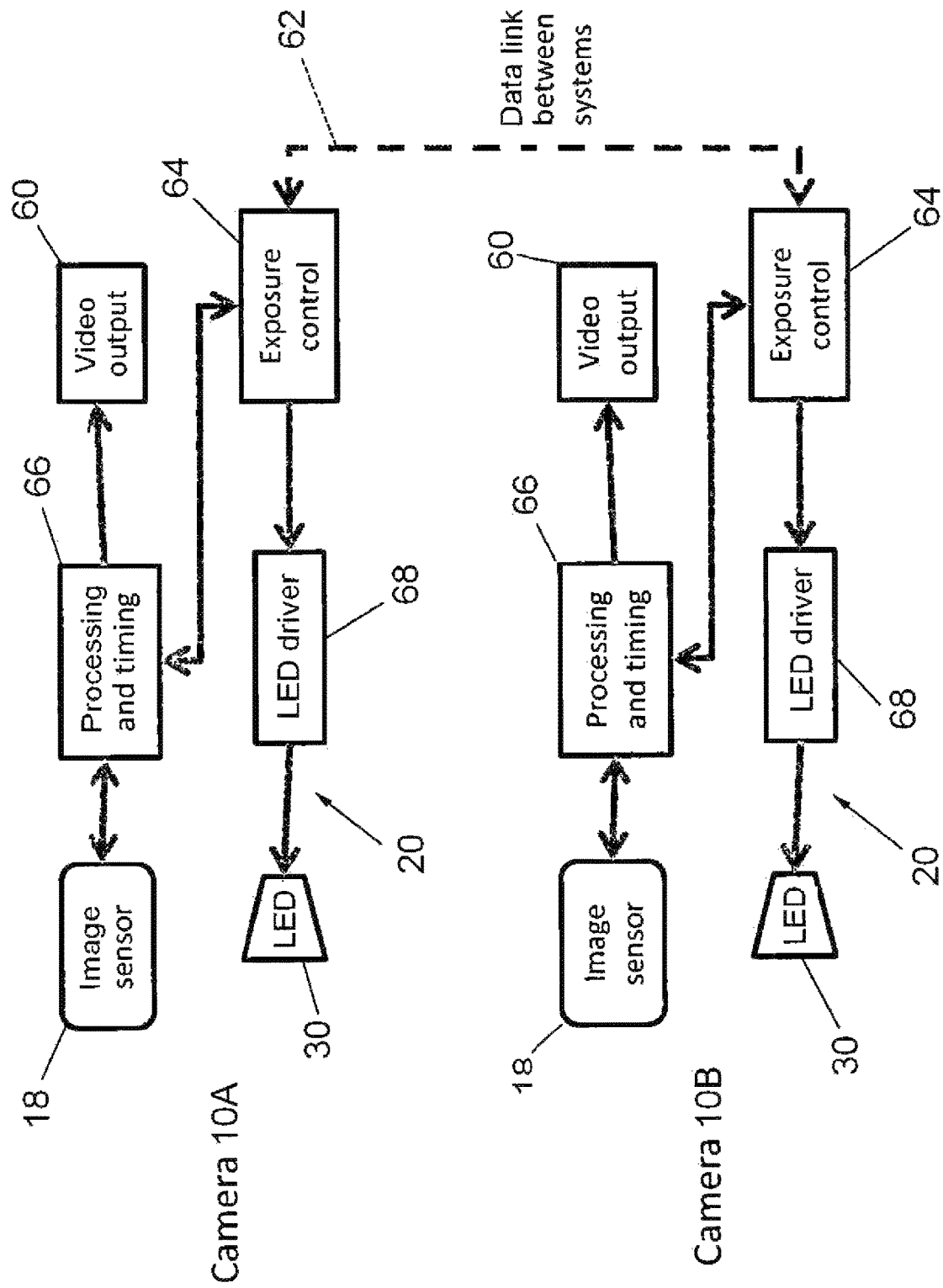
FIG. 4 is a flowchart of a camera system and illumination system for dual endoscopes.

In addition to the processing elements 48, 58, functionally identified in FIG. 4 as exposure control 64 and processing and timing 66, the video cameras 10 each include the image sensor 18, a video output function 60, and the light source 20 with an LED lamp 30 and an LED driver 68. The data link 62 is connected between the video cameras 10 to the exposure control 64. Provision for wire or RF coupling are added to traditional camera control unit 14 for the data link 62. Each of the exposure controls 64 has a video capture profile of the image sensor frame rate, a sequence of the selected frame images and light source duration for the exclusive activation of each of respective frame memories. In spite of the physical and electronic components of FIGS. 1 through 5, the camera control units, the video output 60, the exposure control 64 and the processing and timing 66, appearing as separate units, other contemplated arrangements include combining such elements physically and/or electronically and also to run the diverse functions of each camera and light source 20 in integrated CCU. In doing so, the control units 14 and the data link 62 form a control system for the assembly of endoscopes.

Figure 5:
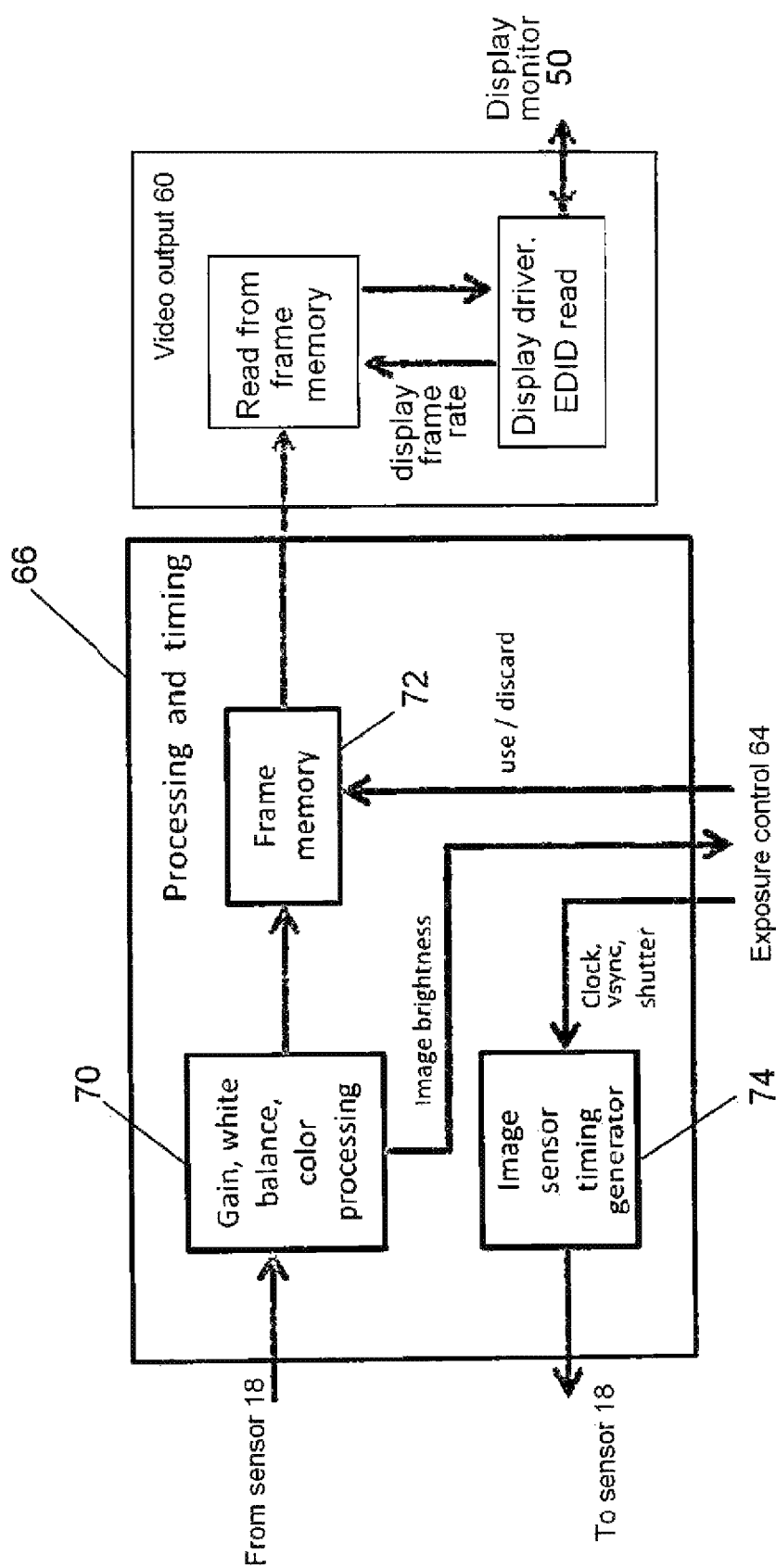
FIG. 5 is a flowchart of the functional aspects of processing and timing associated with each video camera.

FIG. 5 illustrates the functional aspects of processing and timing 66 associated with each video camera 10. The image sensors 18 are driven at a preselected and synchronized video frame rate by a timing generator 74. The sensor video frame rate may be common to both cameras 10; or one may be an integer multiple of the other. The image sensors 18 transmit all video image frames to processing and timing 66 at a preselected video frame rate. A frame processing function 70 applies corrections to the transmitted images and directs selected images from the image sensors 18 to a frame memory function. As with the other electronic elements, the frame memories 72 of the cameras 10 may be found in each camera 10, respectively, in one physical unit or at separate locations in one memory device. The memory collecting functions and distribution functions through the video output or outputs 60 to a split display or displays 50 remain dedicated to respective cameras 10. This dedication is to be understood and referred to in spite of the physical and electronic arrangement with reference to the displays 50, video outputs 60, and frame memories 72 in the Specification and claims.

In the frame processing function 70, there also is the white balance process to correct for color variation of the illumination light to assure accurate color reproduction. As with traditional endoscopic cameras, each camera 10 is white balanced by the user while imaging a white target. Only the light source associated with the camera undergoing the white balance process is illuminated during white balance. The frame processing function 70 also provides image brightness measurement which is directed to exposure control 64. Image brightness is calculated from the pixel values produced by the image sensor for each frame. These are the same pixel values that make up the image. The result is used to choose exposure settings for the next frame. Exposure settings may be image sensor exposure duration, light source intensity or light source ON duration.

The frame memory 72 either discards or reserves the incoming normalized frame images according to the preselected pattern of exposure control 64. The reserved frame images are then communicated to the video output 60. The display 50 typically requires 60 frames/second. Because of the discarded frame images, a new frame image may not be available for every required frame at the display. The video output 60 uses frame rate conversion to present the last received selected frame image from the frame memory 72 at the required frame rate of the display 50. The display 50 may also be combined into one split screen monitor receiving multiple signals from the video output or outputs 60.

Figure 6:
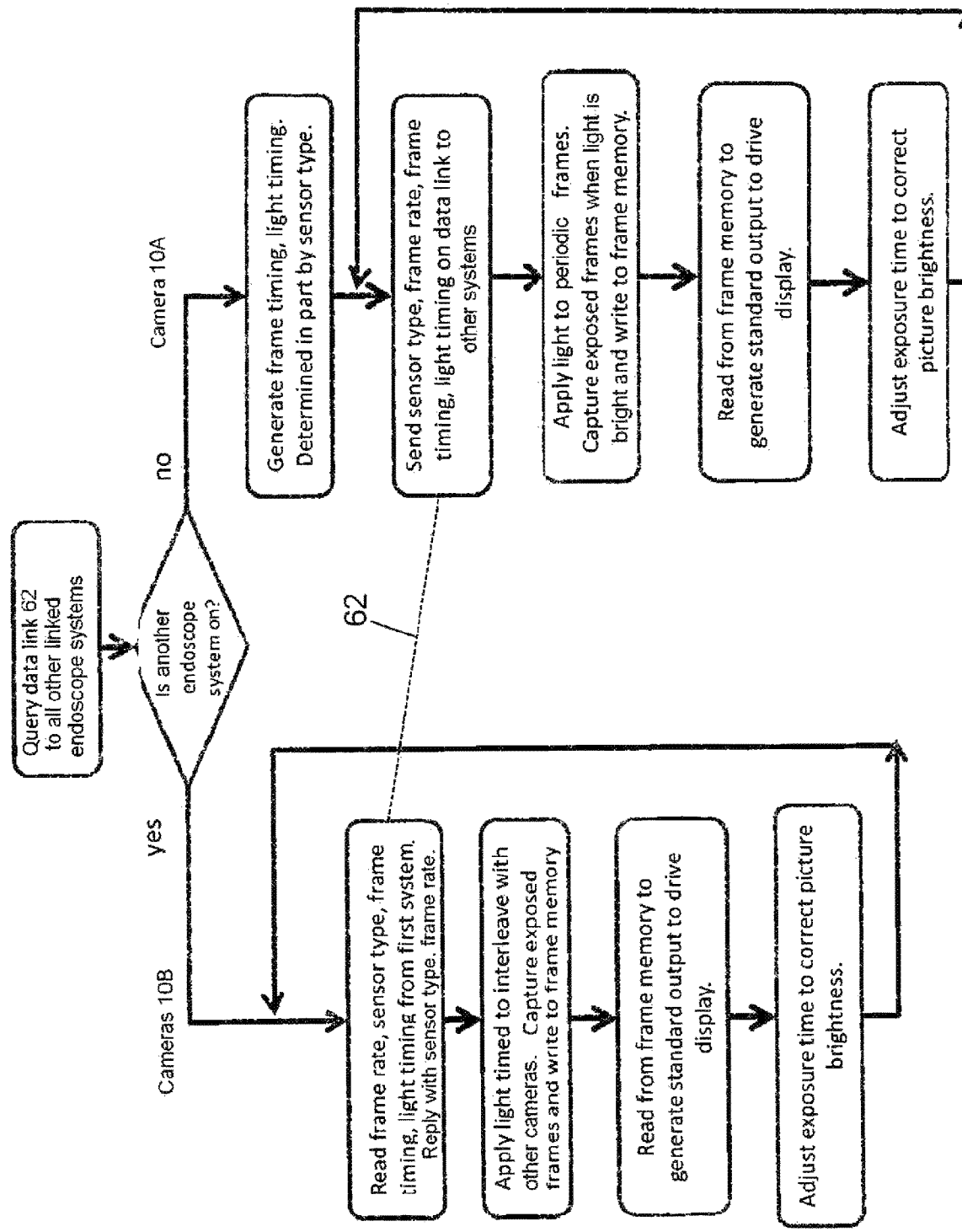
FIG. 6 is a logic diagram of the control and timing of the cameras and light sources of multiple cameras.
Figure 8:
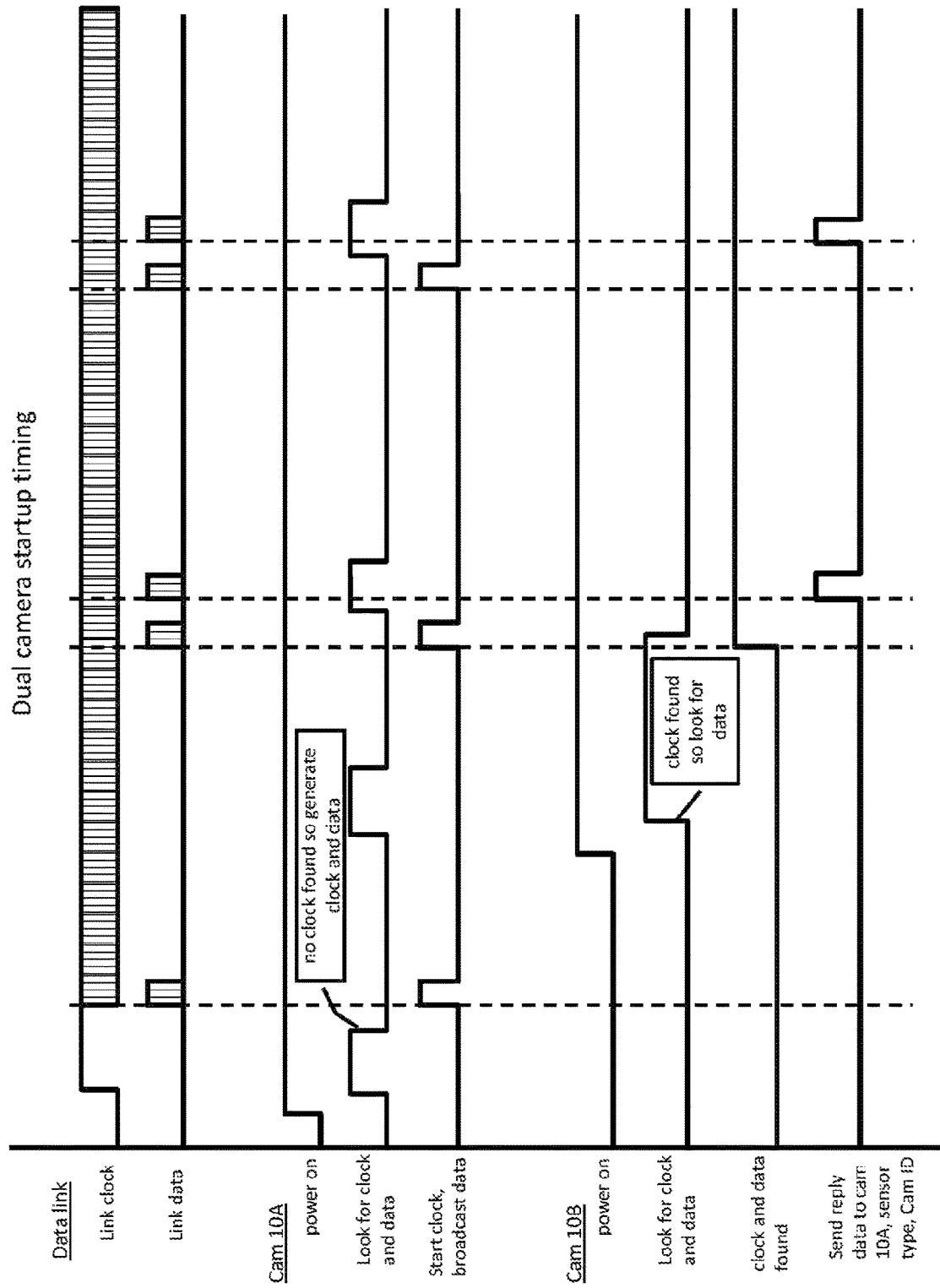
FIG. 8 is a control timing diagram for the startup of the example explanatory exposure timing diagram of FIG. 10 with the active state for the signal being the upper position.

FIG. 6 illustrates the logic process for effecting the timing and activation of multiple endoscopic cameras 10. The process generates concurrent videos without light interference between cameras 10, useful in a surgical setting. To initiate the process, data linked endoscopic cameras 10 are turned on. Each camera will query the status of the other one or more linked cameras 10. The cameras 10 will defer to the first to register as activated, which then becomes the lead camera. Each of the cameras 10 may be programmed for the specific camera configurations or may have a variety of stored camera formats which can be selected based on the identification provided by each endoscopic camera. FIG. 8 is a control timing diagram for the startup of the camera arrangement associated with the explanatory exposure timing diagram of FIG. 10.

Figure 9:
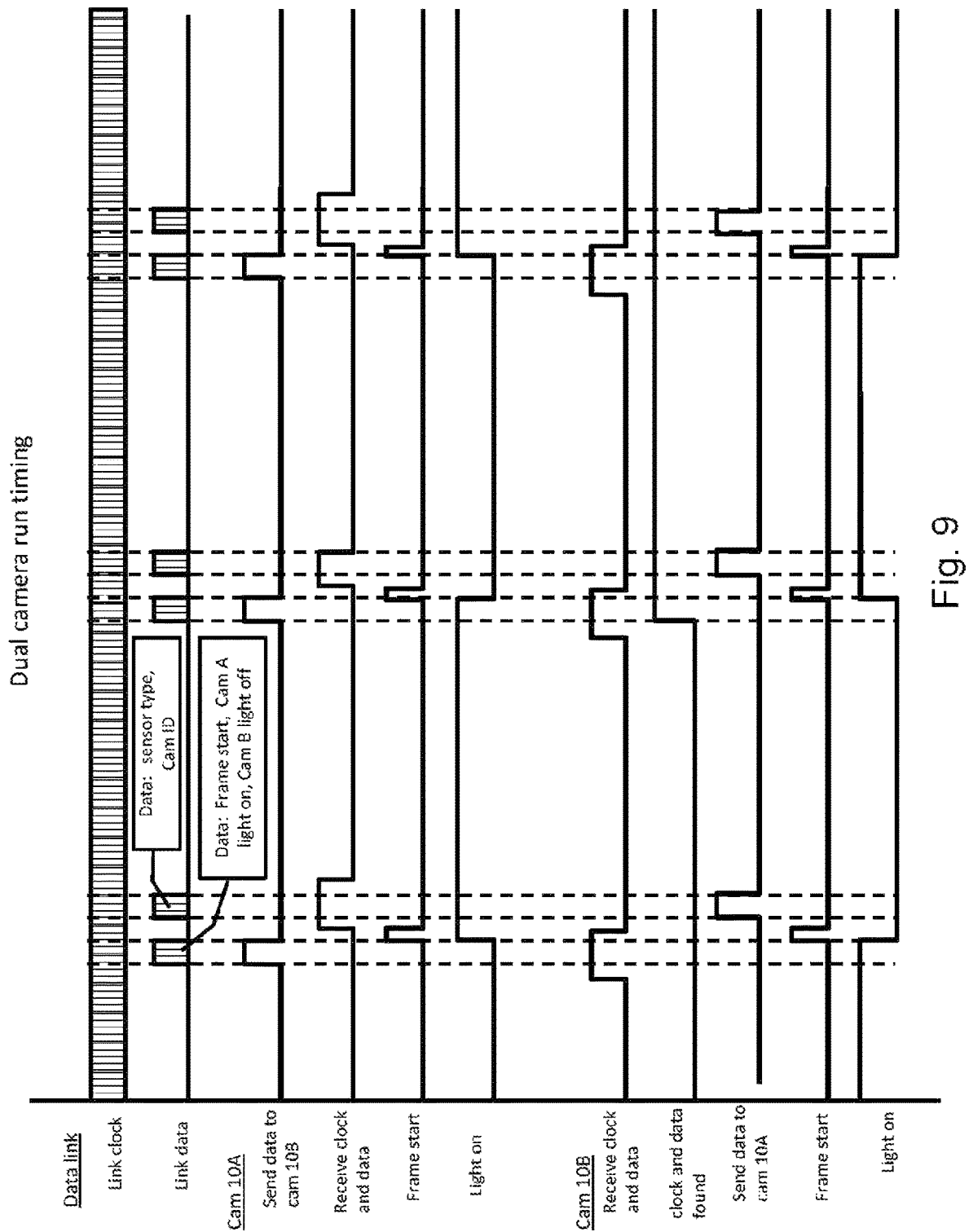
FIG. 9 is a control timing diagram for the continuing operation of the example explanatory exposure timing diagram of FIG. 10 with the active state for the signal being the upper position.

To begin, the lead camera 10A, with recognition of the formats of the other linked cameras 10, will define the order for the initiation of each camera exposure control 64 to activate each respective frame memory 72 and light source 20. Each activation is "exclusive" such that no two light sources 20 provide direct lighting at the same time. The term "direct lighting" is here used to denote lighting that is aligned with the associated camera 10 to illuminate the field of view of that camera. Having the direct lighting operating exclusively prevents the light source 20 from one linked endoscope overexposing a selected image frame of a field of view captured by another of the linked endoscopes. In turn, the respective light source 20 is timed to properly illuminate the field of view for the selected image frame or sequential image frames exclusively recorded. In steps once the first camera 10A has been established in the lead, the second camera 10B comes online and broadcasts its preferred sensor information on the data link 62. Referring to FIG. 9, at the end of a frame exposure the first camera 10A switches its own light source 20 OFF and sends a signal to the other camera 10B to turn its light source 20 ON and begin exposing a frame. The camera clocks are synchronized, meaning they effectively operate from the same timing source through the data link 62. When the frame exposure of the second camera 10B is complete and its light source 20 is turned OFF, the first camera light source 20 will turn on again to expose its next frame, and the cycle repeats. Once the initial synchronization of the frame timing has been made from the first camera 10A to the second camera 10B, the cameras 10 can proceed with only a high-speed clock signal connecting their exposure controls 64. In practice a synchronization signal should be sent at the frame rate to the second camera 10B to correct for any intermittent interruptions of the data link 62. Thus, the data link 62 will then continue to allow synchronous operation of each camera exposure control 64 based on the lead camera 10A. FIG. 9 is a control timing diagram for the continuing operation of the camera arrangement associated with the explanatory exposure timing diagram of FIG. 10.

The synchronized routines performed by the exposure control 64 of the lead camera 10 and the camera exposure controls 64 of each camera 10 tracking in repeated serial order is illustrated in FIG. 6. Each camera 10 drives the image sensors 18 at the preselected frame rate. Each camera exposure control 64 activates the light source 20 and captures the selected image frame or frames of the illuminated field of view in the frame memory 72. The selected camera images captured by each camera 10 are read and transformed by frame rate conversion into a standard output to a display 50 dedicated to each camera 10, respectively. A continuing video is thus created over successive image selections. Additionally, a shutter driver of an exposure system monitoring picture brightness adjusts the exposure period of the image profile. Alternatively, the exposure control 64 may modulate light intensity or light source ON duration.

Figure 7:
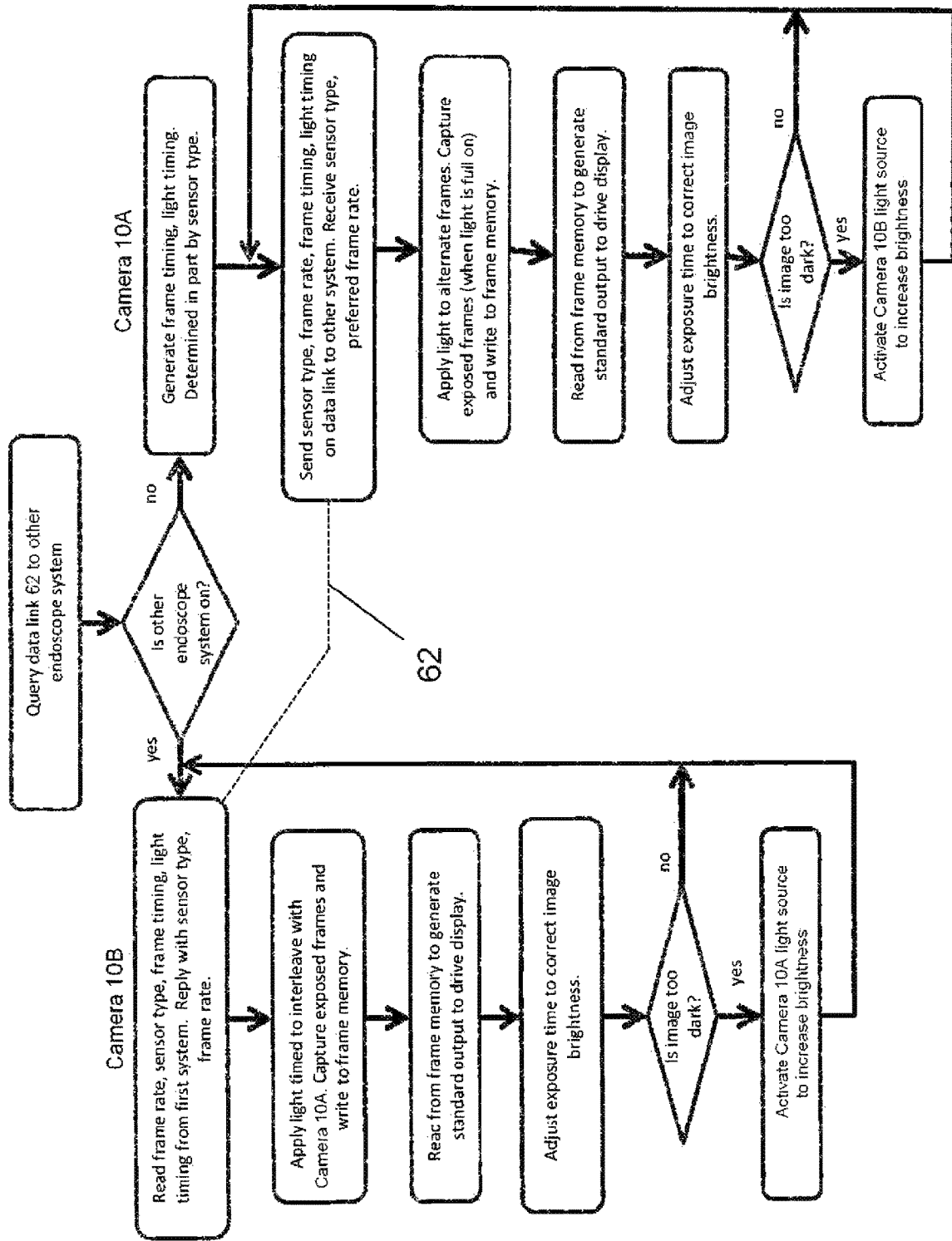
FIG. 7 is a logic diagram of the control and timing of the cameras and light sources of multiple cameras with supplementary background illumination.
Figure 18:
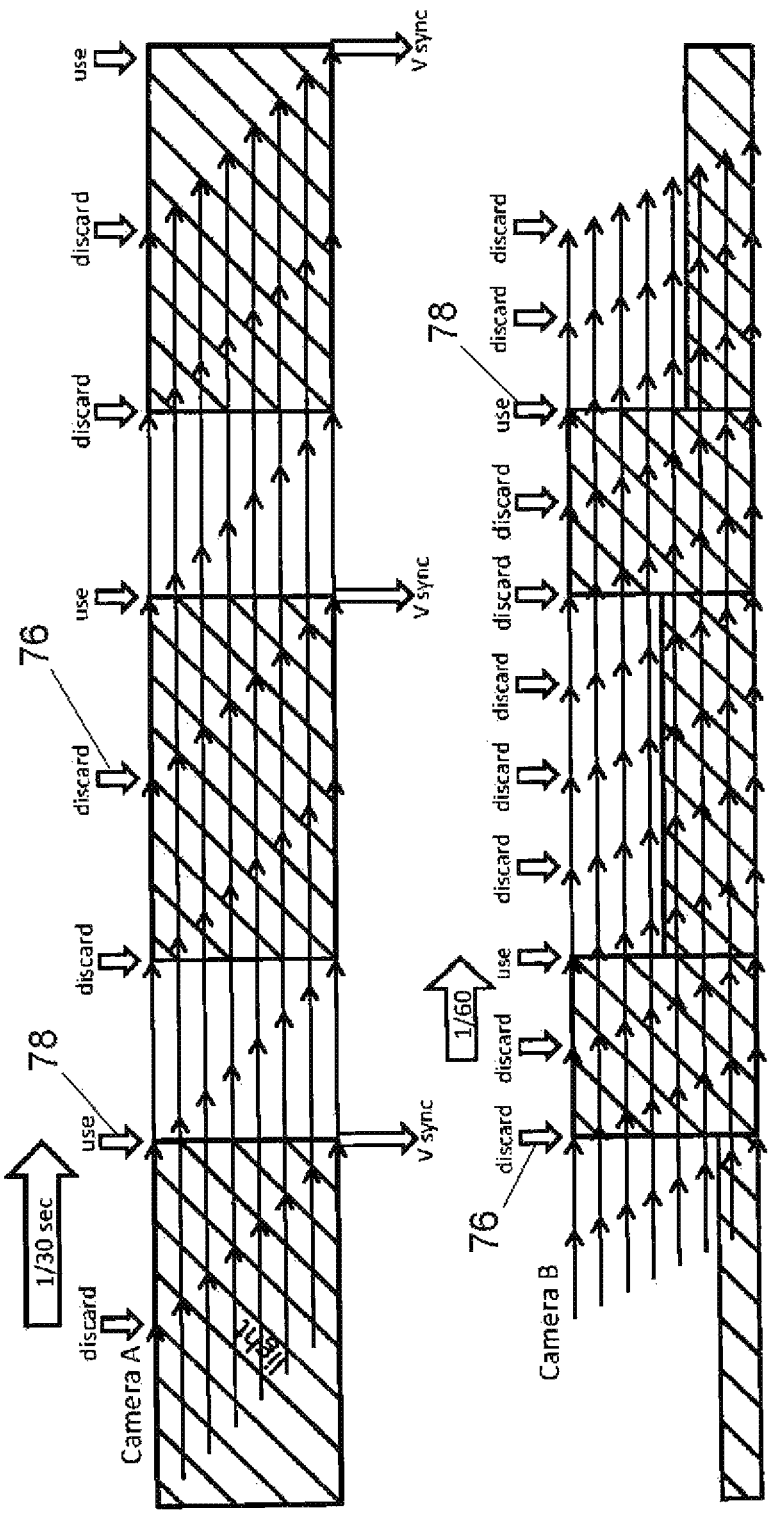
FIG. 18 is an explanatory exposure timing diagram of two cameras with controlled activation of video frame image selection and light source with both cameras use a rolling shutter with the cameras at different frame rates; and one light source includes direct lighting and supplemental background lighting.

FIG. 7 illustrates the logic process for effecting the timing and activation of multiple endoscopic cameras 10 with both direct lighting and supplementary background illumination. The process generates concurrent videos with minimal light interference between cameras 10. This is useful in a surgical setting where direct lighting from the light source associated with the capturing camera is not sufficient to produce an acceptably exposed image. Supplementary illumination mode as shown in FIGS. 7 and 18 differs from the normal mode of FIG. 6 in that a light source other than the one associated with the camera capturing an image is ON. The process, controlled by the exposure control 64 of each camera 10 operates as described above and as shown in FIG. 7 until the exposure is corrected by one of changing frame exposure time, light source intensity or light source ON duration.

A first order process simply turns off all but the direct lighting of the light source 20 associated with the camera 10 capturing selected frame images, a first "mode". However, need for supplemental lighting can be accommodated by modulating the light source or sources 20 associated with the camera or cameras 10 not concurrently capturing selected frame images in the system of FIG. 7, a second "mode". If the exposure correction is unable to provide adequate brightness or clarity to the image, background lighting is provided by the light source or sources 20 with the camera or cameras 10 not concurrently capturing selected frame images through this second "mode". The term "background lighting" is used here to denote light from the light sources 20 of the camera or cameras 10 not concurrently capturing selected frame images. In this second mode, the light sources would preferably provide a light intensity substantially reduced from that of the direct lighting as supplementation. If the intensity of the background lighting interferes with the frame image capture associated with the direct lighting, the background lighting would not be called for or would be cancelled. The modulated background lighting may be a simple responsive ON/OFF or a stepped modulation responsive to repeated calculated image brightness. Indeed, some preference may be given to starting with the camera or cameras 10 not concurrently capturing selected frame images providing a selected low intensity of background lighting as the starting point before modulation, estimated to begin at 20% of exposure intensity.

The background lighting will have varying effect based on the relative positioning of the distal ends of the endoscopes. If the viewing and lighting angle between endoscopes is less than 90°, the two endoscopes will possibly provide complementary light toward the field of view. At obtuse angles, the background lighting may not brighten the field of view but provide more light intensity to the image sensor. This would normally be a disfavored result. Therefore, it can be most advantageous to use a camera graphical user interface (GUI) to manually control the second mode of operation. The operator can then manipulate the orientation of the endoscopes in conjunction with control of the background mode. An automatic second mode using a slower exposure control feedback loop may also be used as the operator can better control the video by reorienting the relative positions of the endoscopes.

FIGS. 10 through 18 illustrate exposure timing diagrams of endoscopic camera image sensors with controlled activation of video frame image selection and light source. The image sensors 18 continuously generate video frame images of the field of view at a fixed video frame rate. These frame images are indicated by both "discard" arrows 76 and "use" arrows 78 at the top of each camera exposure timing diagram in these figures. The camera exposure control 64 of each camera captures selected frame images in the frame memory as indicated by the use arrows 78. The remainder are discarded as indicated by the discard arrows 76. The arrow positions indicate the end of exposure for the last line of a of a particular frame. This does not necessarily coincide with the output of that frame by the image sensor. Looking at each set of two or three data linked cameras 10 in each of the diagrams, the camera exposure controls 64 are shown to capture to the frame memories one or more frame images in recurring serial order. The timing is synchronized by the lead camera 10 through the data link as discussed above. The camera exposure controls 64 also can control frame image exposure duration.

The light sources 20 are also synchronized as to timing and duration by the camera exposure controls 64. Each light source 20 is exclusively activated to coincide with the generation of video frame images by the associated image sensor 18 that are to be selectively captured in the associated frame memory 72. This exclusive activation occurs in recurring serial order as well to provide the light needed for proper frame exposure. To avoid chance overexposure, each light source 20 is deactivated when another of the data linked cameras 10 is generating video frame images by its own associated image sensor 18 that are to be selectively captured in its associated frame memory 72. The camera exposure controls 64 also may be employed to control light source activated duration and brightness to maintain proper exposure.

Figure 10:
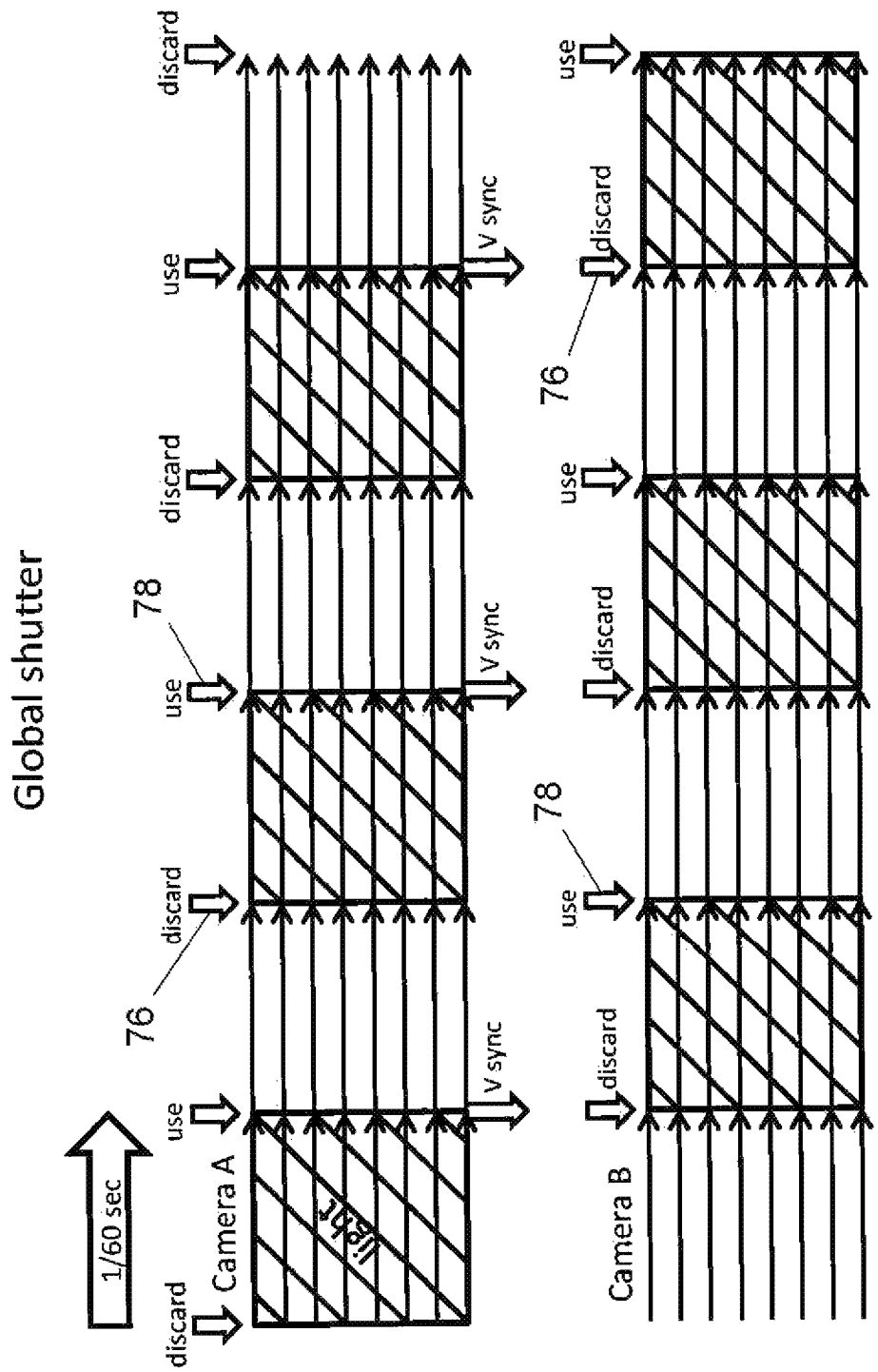
FIG. 10 is an explanatory exposure timing diagram of two cameras with controlled activation of video frame image selection and light source with both cameras using global shutters.

The timing synchronization is straight forward with two global shutter image sensors, as shown in FIG. 10. Alternate frame images sensed by each camera image sensor 18 are selected for retention by the frame memory 72 in recurring serial order. With two cameras, the selected retention by the frame memory 72 is simply recurring alternation. The light source 20 is shown (diagonal shading) to be activated during generation of the video images to be selectively captured by the frame memory 72 for use in the resulting video. Thus, the selection of frames alternates; and the frame rate and timing are synchronized along with activation of the light source. With frame rate conversion, each of two displays 50 will receive an original and copy of each selected frame image of the respective field of view to create a continuous video image from each camera 10. The image update rate for global shutter image sensors in FIG. 10 is 30 fps for a video system operating at a preselected frame rate of 60 fps.

Figure 11:
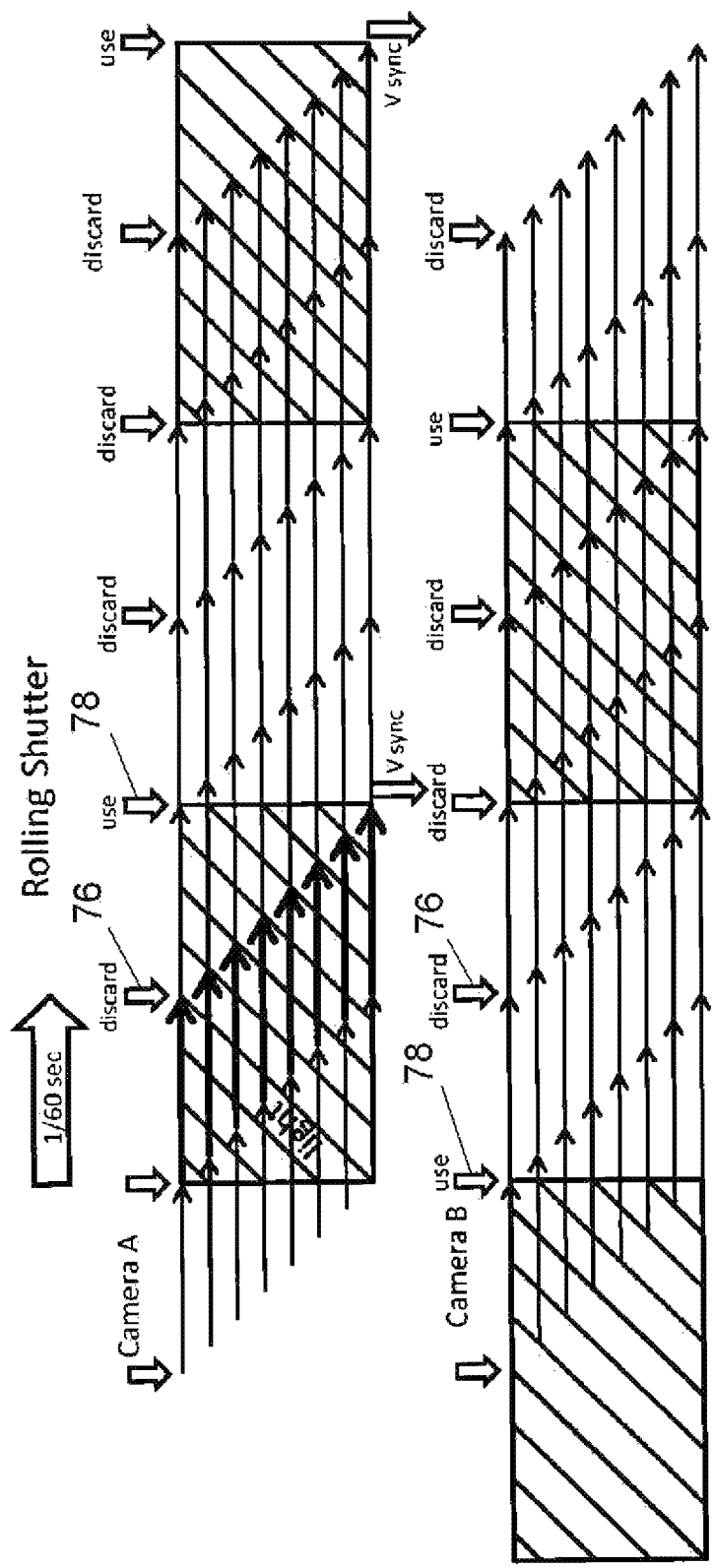
FIG. 11 is an explanatory exposure timing diagram of two cameras with controlled activation of video frame image selection and light source with both cameras using rolling shutters.

Using an image sensor 18 with a rolling shutter slows the frame rate for each camera to half because the sensor requires an extra frame time to generate all raster lines. FIG. 11 illustrates a system using two cameras 10, each with a rolling shutter image sensor 18. Again, alternate frame images sensed by each camera image sensor 18 are selected for retention by the frame memory 72. The light source 20 is shown to be activated during generation of the frame images selected for capture by the frame memory 72. The selection of frames alternates; and the frame rate and timing are synchronized. With frame rate conversion, each of two displays 50 will receive an original and three copies of each selected frame image of the respective field of view to create a continuous video image from each camera 10. The image update rate is 15 fps for a video system operating at a preselected frame rate of 60 fps.

Figure 12:
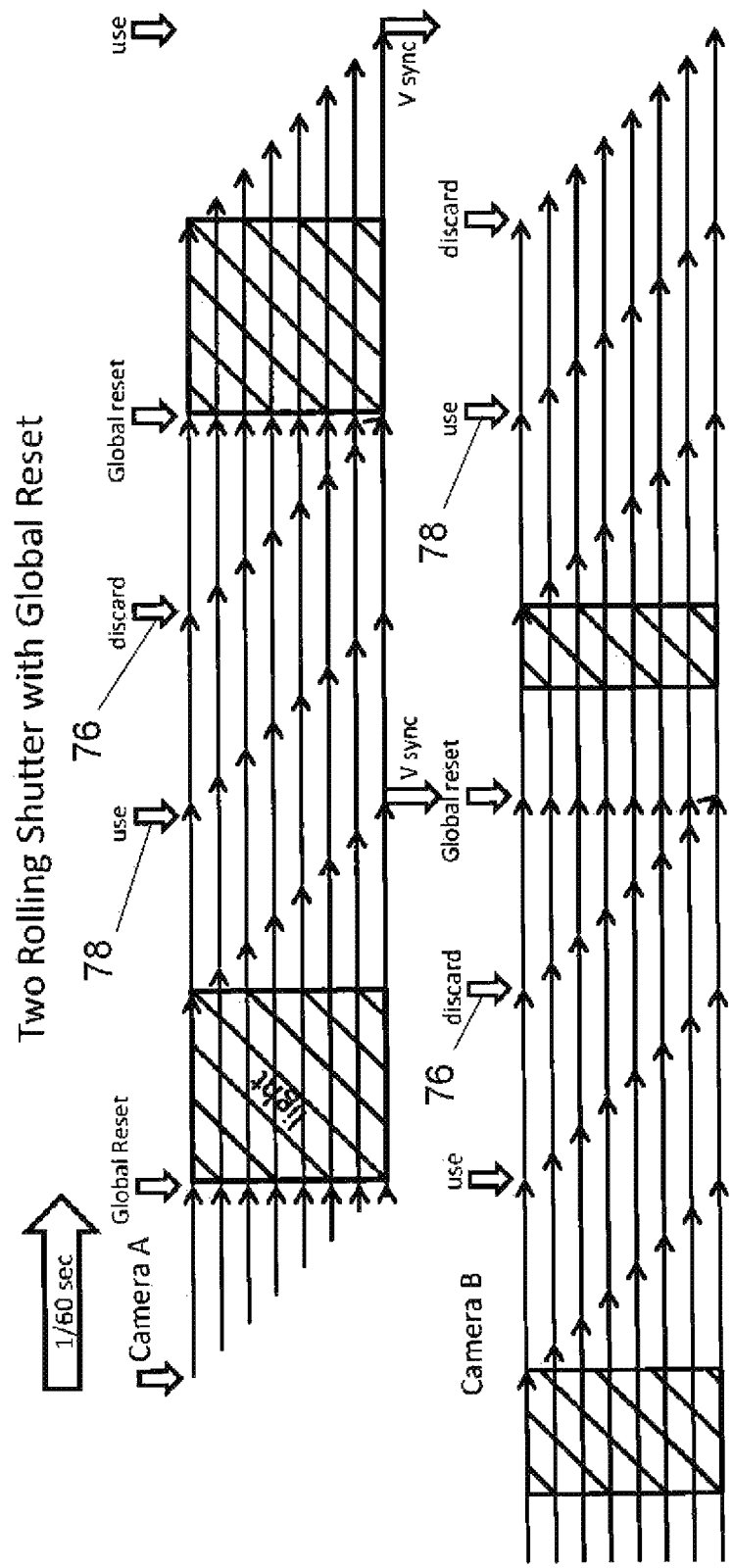
FIG. 12 is an explanatory exposure timing diagram of two cameras with controlled activation of video frame image selection and light source with both cameras using rolling shutters with global reset.
Figure 13:
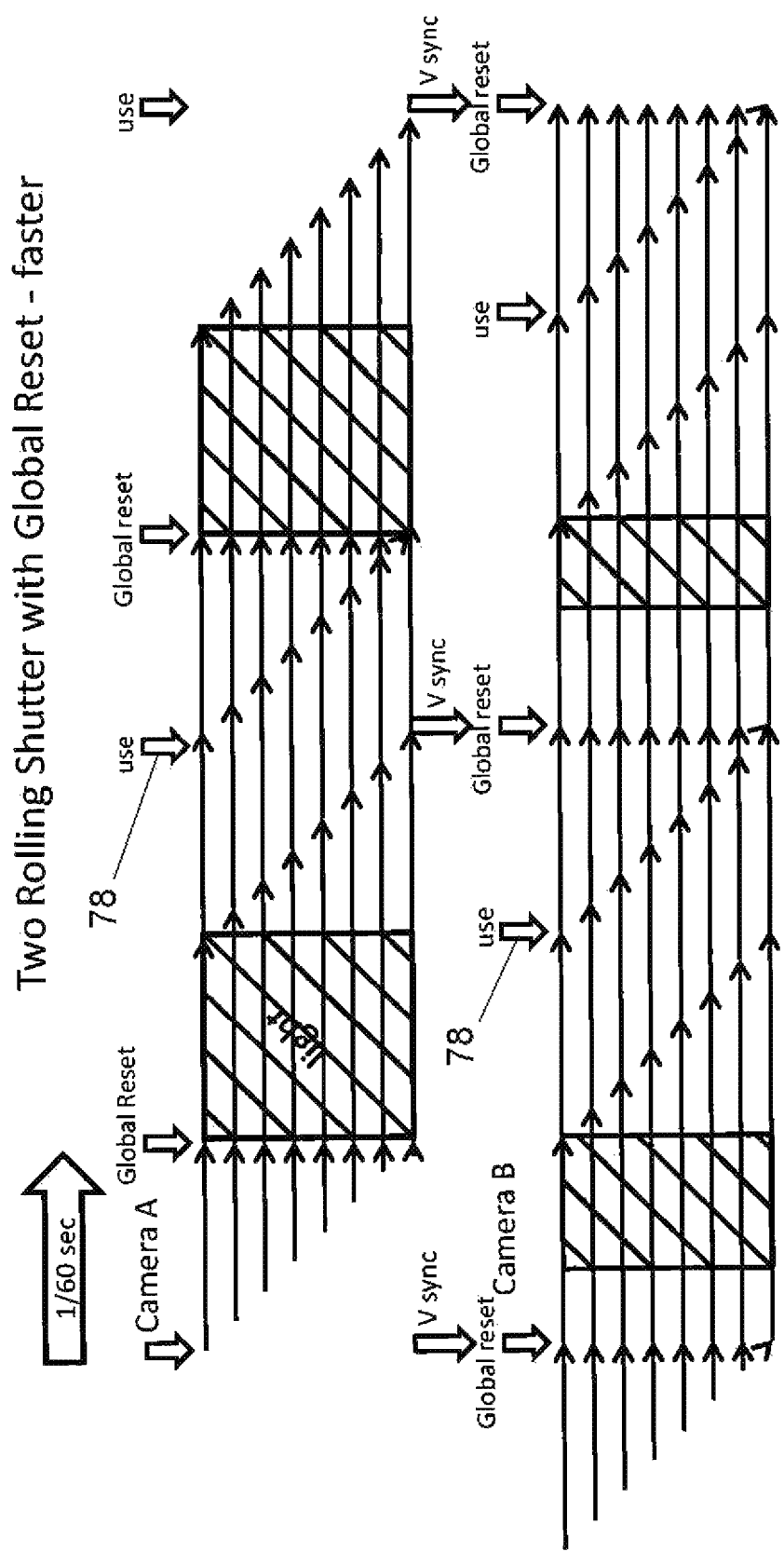
FIG. 13 is an explanatory exposure timing diagram of two cameras with controlled activation of video frame image selection and light source with both cameras using rolling shutters with global reset and an accelerated camera rate.
Figure 14:
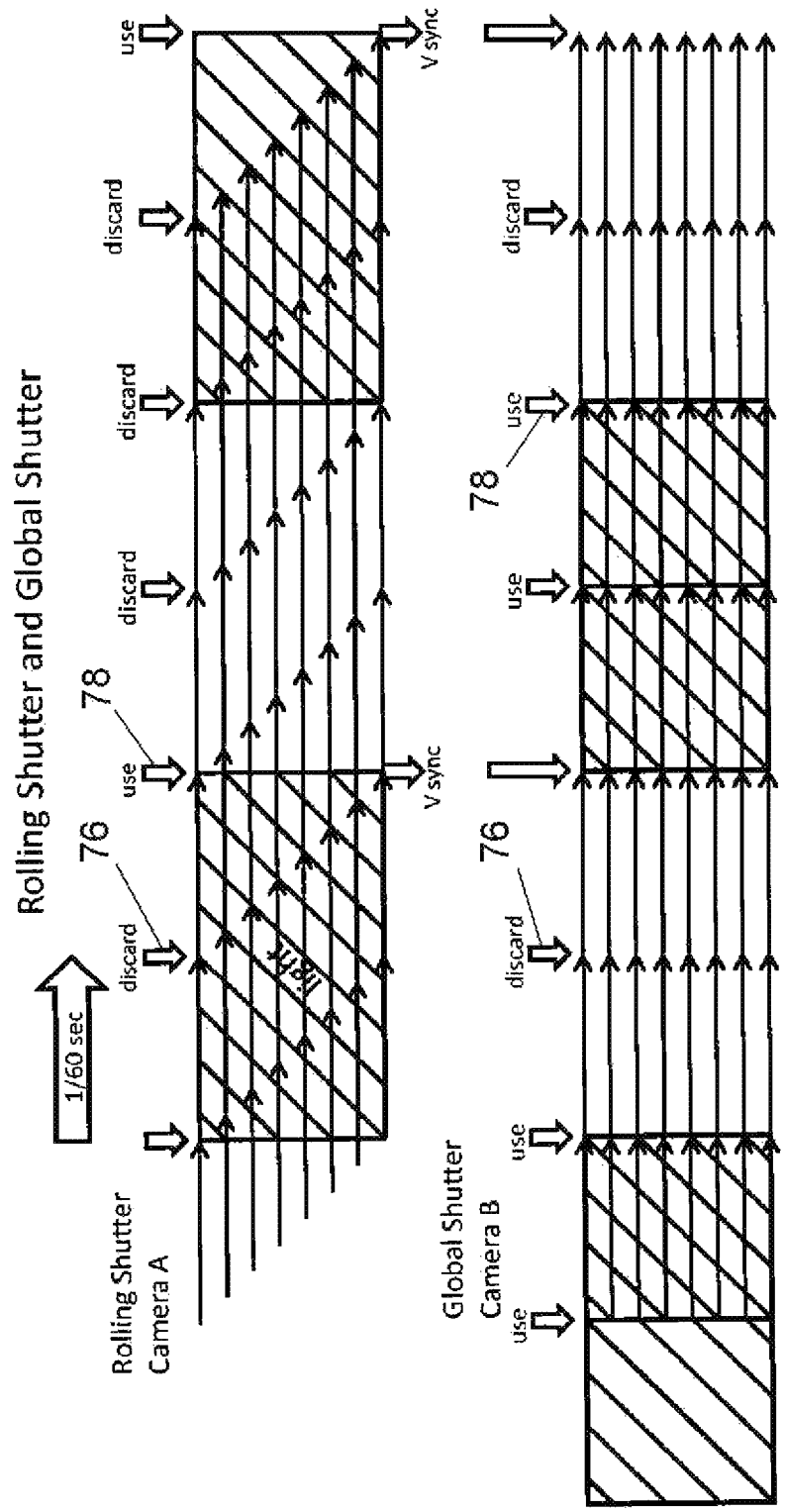
FIG. 14 is an explanatory exposure timing diagram of two cameras with controlled activation of video frame image selection and light source with the first camera using a rolling shutter and the second camera using a global shutter.
Figure 15:
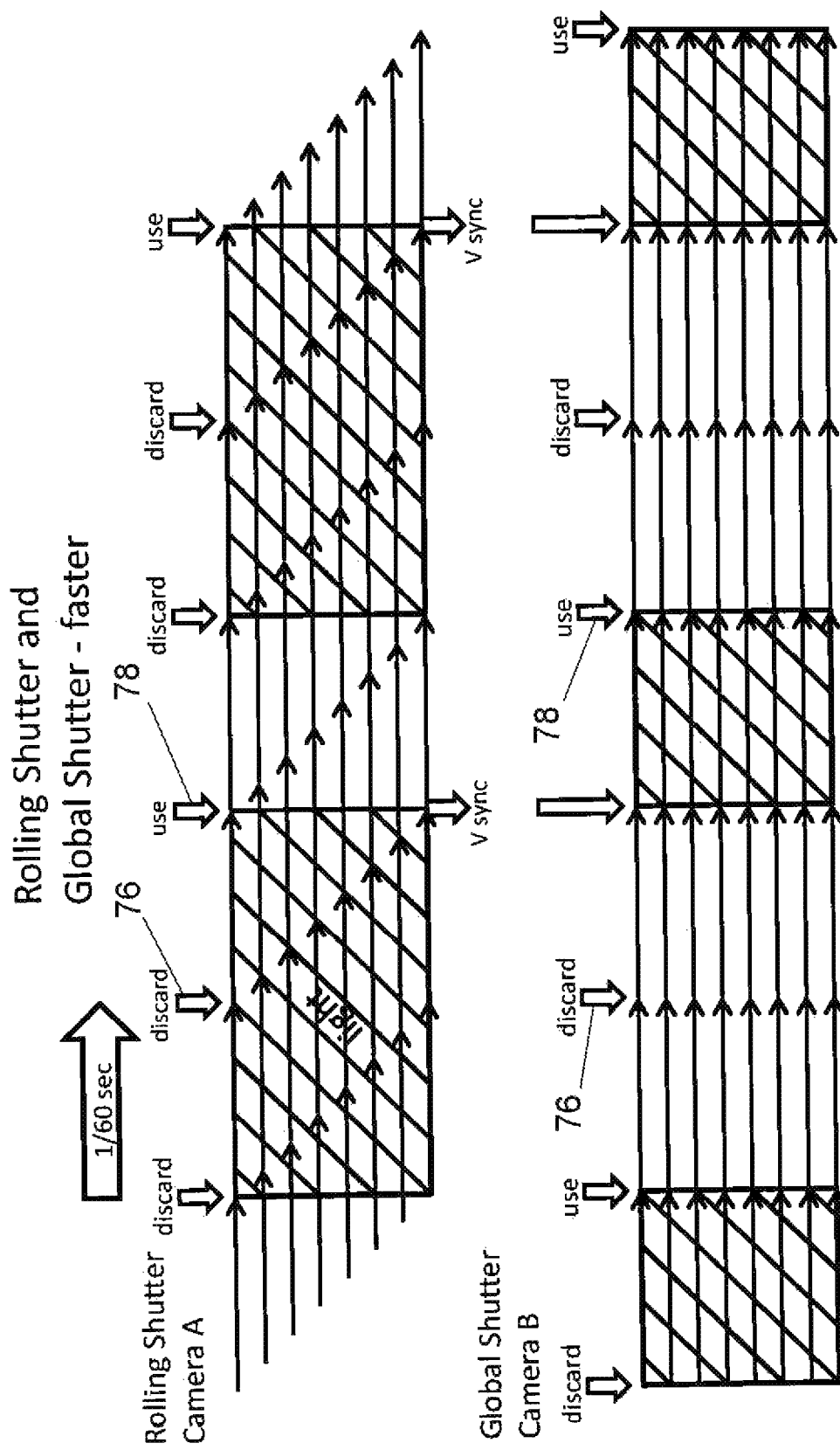
FIG. 15 is an explanatory exposure timing diagram of two cameras with controlled activation of video frame image selection and light source with the first camera using a rolling shutter and the second camera using a global shutter and an accelerated camera rate.
Figure 16:
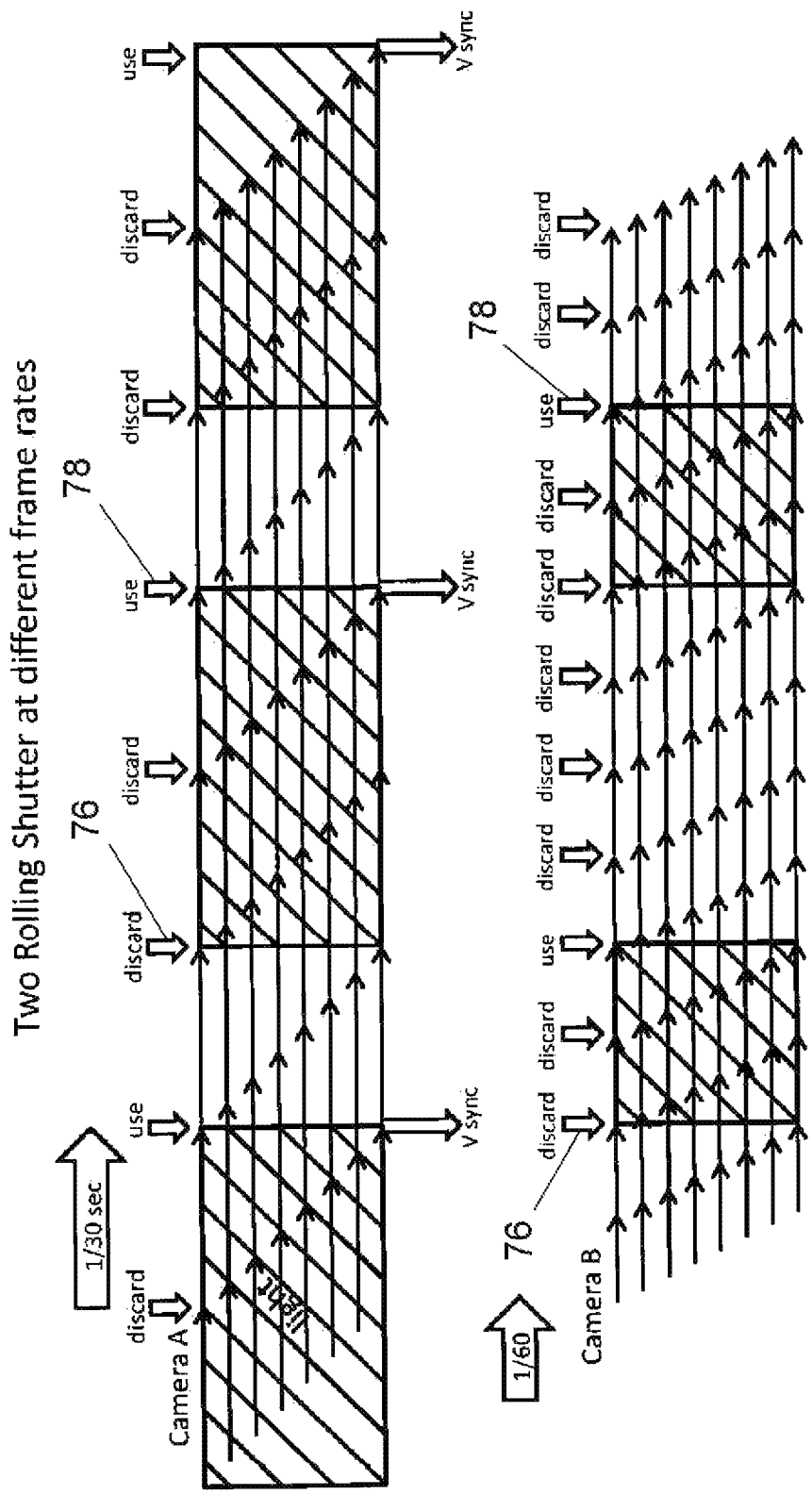
FIG. 16 is an explanatory exposure timing diagram of two cameras with controlled activation of video frame image selection and light source with both cameras use a rolling shutter with the image sensors at different frame rates.
Figure 17:
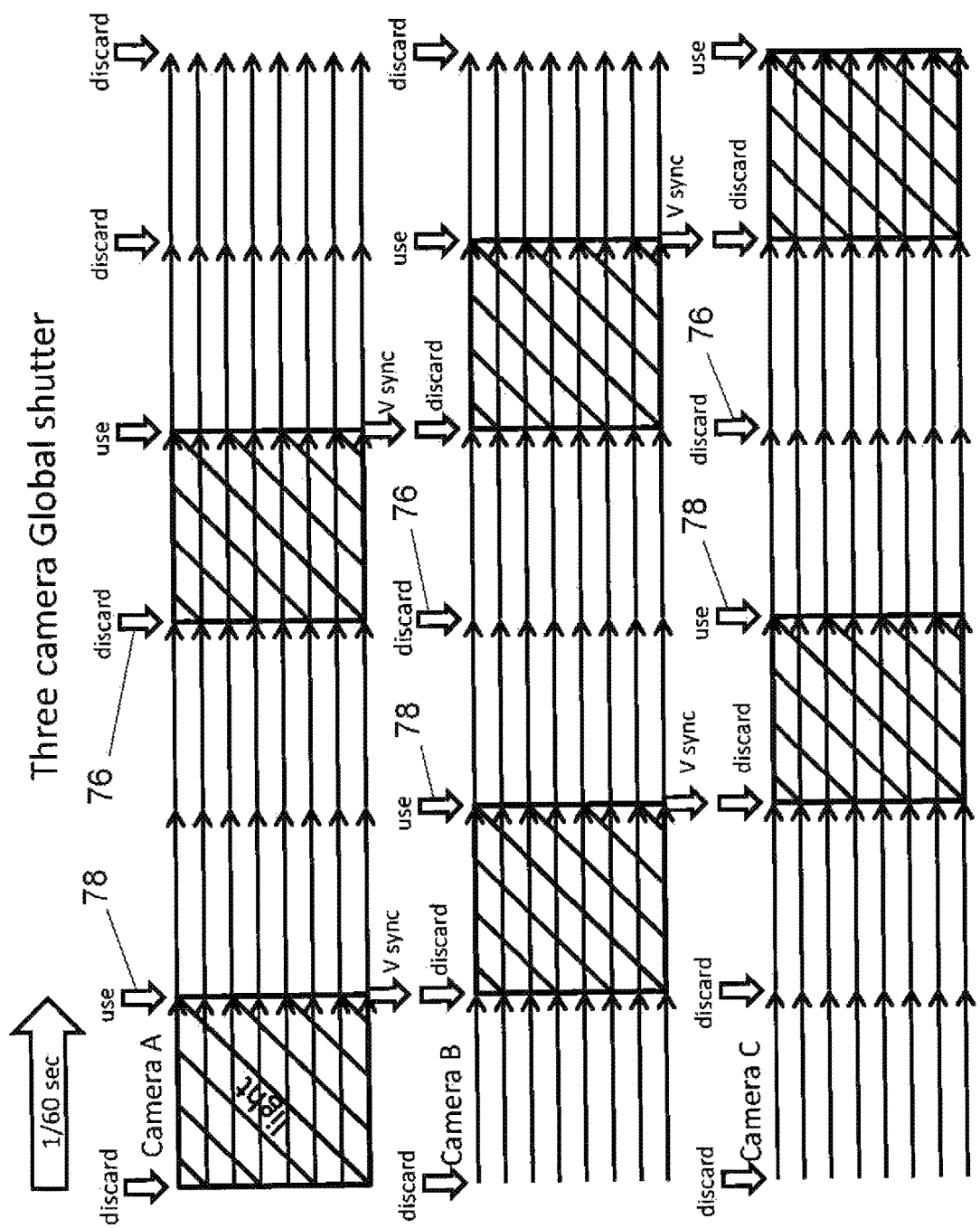
FIG. 17 is an explanatory exposure timing diagram of three cameras with controlled activation of video frame image selection and light source with the three cameras each using a global shutter.

FIGS. 12 through 18 illustrate exposure timing diagrams that represent variations of image sensors 18, image exposure timing and number of sequential images selected for two cameras 10 as identified in each figure beyond those of the more uniform arrangements of FIGS. 10 and 11. The image sensor arrangements show use combinations of global shutters, rolling shutters and rolling shutters with global reset. Variations in exposure control are illustrated in FIGS. 11, 12 and 15. FIGS. 13 and 15 use exposure control to allow an image update rate of 20 fps for a video system operating at a preselected frame rate of 60 fps. FIG. 14 illustrates the selection of sequential frames where a sensor with global shutter must follow the timing of a sensor with rolling shutter. FIG. 16 illustrates one camera 10B operating at an integer multiple frame rate of the other camera 10A. FIG. 17 illustrates an exposure timing diagram for three endoscopes using cameras with global shutters. FIG. 18 illustrates the use of two intensity and timing modes on camera 10B with the arrangement of FIG. 16.

Thus, medical imaging systems are here disclosed which allow the use of multiple illuminating endoscopes with video cameras at a surgical site without light interference. While embodiments and applications of this invention have been shown and described, it would be apparent to those skilled in the art that many more modifications are possible without departing from the inventive concepts herein. The invention, therefore, is not to be restricted except in the spirit of the appended claims.

What is claimed is:

1. A process for using at least two endoscopes in a medical procedure, each endoscope including an image sensor of a respective field of view, a video output and a light source having a first mode of direct lighting of the respective field of view, comprising the steps of
   positioning the endoscopes at a surgical site;
   synchronizing the timing between the image sensors of the at least two endoscopes;
   continuously sensing video frame images with each of the image sensors;
   concurrently selecting and discarding sensed video frame images from the at least two image sensors such that only one of the sensed video frame image from the at least two image sensors is selected at a time;
   activating and deactivating the first modes of the light sources to provide the first mode of direct lighting to illuminate the respective field of view of each of the at least two endoscopes only for each of the selected sensed video frame images;
   communicating the selected video frame images to the respective video outputs.

2. The process of claim 1 further comprising the steps of
   separately saving the selected sensed video frame images from each image sensor, the step of transmitting the selected video frame images including transmitting the last saved selected video frame image of each saved selected sensed video image;
   communicating the selected video frame images to the respective video outputs.

3. The process of claim 1, the light sources of each of the at least two endoscopes having a second mode of background lighting, further comprising the step of illuminating the respective fields of view of the unselected sensed video frame images with the second mode background lighting of the light sources of each of the endoscopes.

* * * * *